(12) United States Patent
Frick et al.

(10) Patent No.: US 11,690,999 B2
(45) Date of Patent: Jul. 4, 2023

(54) ELECTRODE DEVICE AND A NEEDLE ELECTRODE FOR USE IN DELIVERY OF ELECTRICAL PULSES TO A DESIRED TISSUE OF A MAMMAL

(71) Applicant: SCANDINAVIAN CHEMOTECH AB, Lund (SE)

(72) Inventors: Mohan Frick, Gothenburg (SE); Bertil RR Persson, Lund (SE); Johan Marnfeldt, Malmo (SE)

(73) Assignee: Scandinavian Chemotech AB, Lund (SE)

( * ) Notice: Subject to any disclaimer, the term of this patent is extended or adjusted under 35 U.S.C. 154(b) by 620 days.

(21) Appl. No.: 16/633,347

(22) PCT Filed: Jul. 27, 2018

(86) PCT No.: PCT/EP2018/070440
§ 371 (c)(1),
(2) Date: Jan. 23, 2020

(87) PCT Pub. No.: WO2019/020801
PCT Pub. Date: Jan. 31, 2019

(65) Prior Publication Data
US 2021/0154467 A1    May 27, 2021

(30) Foreign Application Priority Data

Jul. 28, 2017 (SE) .................................. 1750965-4

(51) Int. Cl.
*A61N 1/04* (2006.01)
*A61N 1/05* (2006.01)
*A61N 1/32* (2006.01)

(52) U.S. Cl.
CPC ......... *A61N 1/0416* (2013.01); *A61N 1/0412* (2013.01); *A61N 1/0424* (2013.01);
(Continued)

(58) Field of Classification Search
CPC .. A61N 1/0412; A61N 1/0416; A61N 1/0424; A61N 1/0472; A61N 1/0502;
(Continued)

(56) References Cited

U.S. PATENT DOCUMENTS 5,674,267 A    10/1997  Mir et al.
2002/0151866 A1  10/2002  Lundkvist et al.
(Continued)

FOREIGN PATENT DOCUMENTS

EP        3187138 A1    7/2017
KR   10-2016-0145184 A   12/2016
(Continued)

OTHER PUBLICATIONS

Office Action issued in related Swedish Application No. 1750965-4, dated Mar. 16, 2018.
(Continued)

*Primary Examiner* — Amanda K Hulbert
(74) *Attorney, Agent, or Firm* — Merchant & Gould P.C.

(57) ABSTRACT

An electrode device for use in delivery of electrical pulses to a desired tissue of a mammal. The electrode device comprises a handle portion comprising first second electrode connections, and first and second needle electrodes comprising a respective first and second attachment end. Each one of the first and second electrode connections is configured with an inner electrode position and an outer electrode position, wherein the inner and outer electrode positions are electrically conducting. Further, each one of the first and second attachment ends is configured with an insulating part configured to electrically insulate one out of the inner electrode position and the outer electrode position when located therein, and configured with an electrically conducting part configured to conduct current supplied to the other one out of the inner electrode position or the outer electrode position when located therein.

21 Claims, 9 Drawing Sheets

(52) U.S. Cl.
CPC ......... *A61N 1/0472* (2013.01); *A61N 1/0502* (2013.01); *A61N 1/327* (2013.01)

(58) Field of Classification Search
CPC ........ A61N 1/327; A61N 1/00; A61N 1/0404; A61N 1/0476; A61N 1/048; A61N 1/36002; A61N 1/36017
See application file for complete search history.

(56) References Cited

U.S. PATENT DOCUMENTS

| | | |
|---|---|---|
| 2005/0052630 A1 | 3/2005 | Smith et al. |
| 2005/0171574 A1 | 8/2005 | Rubinsky et al. |
| 2008/0091135 A1 | 4/2008 | Draghia-Akli et al. |

FOREIGN PATENT DOCUMENTS

| | | |
|---|---|---|
| WO | 99/52589 A1 | 10/1999 |
| WO | 2011/056464 A2 | 5/2011 |
| WO | 2015/175570 A1 | 11/2015 |
| WO | 2017/117508 A1 | 7/2017 |

OTHER PUBLICATIONS

International-Type Search Report issued in related Swedish Application No. 1750965-4, dated Mar. 16, 2018.
International Search Report issued in related International Application No. PCT/EP2018/070440, dated Jan. 9, 2019.
Swedish Search Report from corresponding Swedish Application No. 1750965-4, dated Mar. 16, 2018.

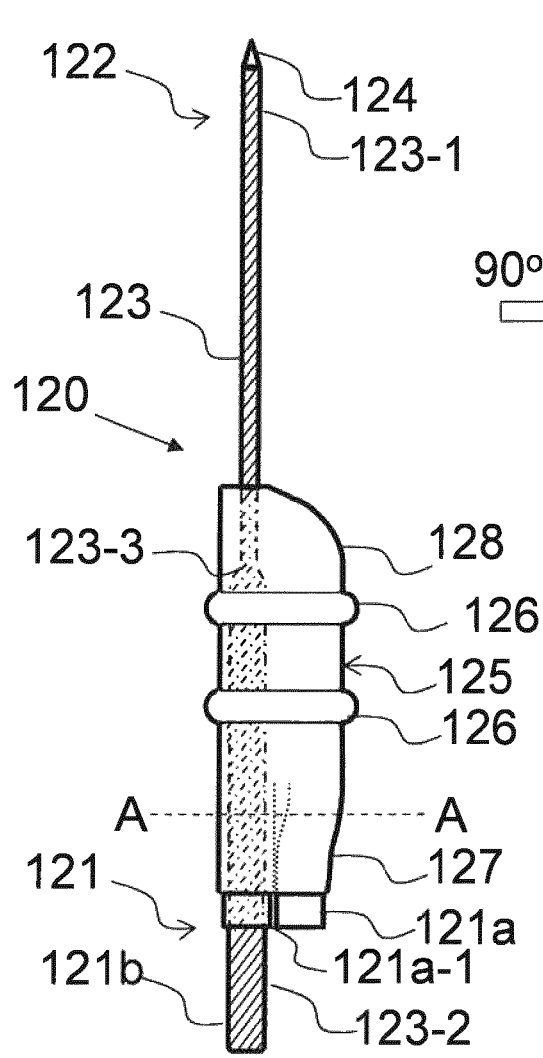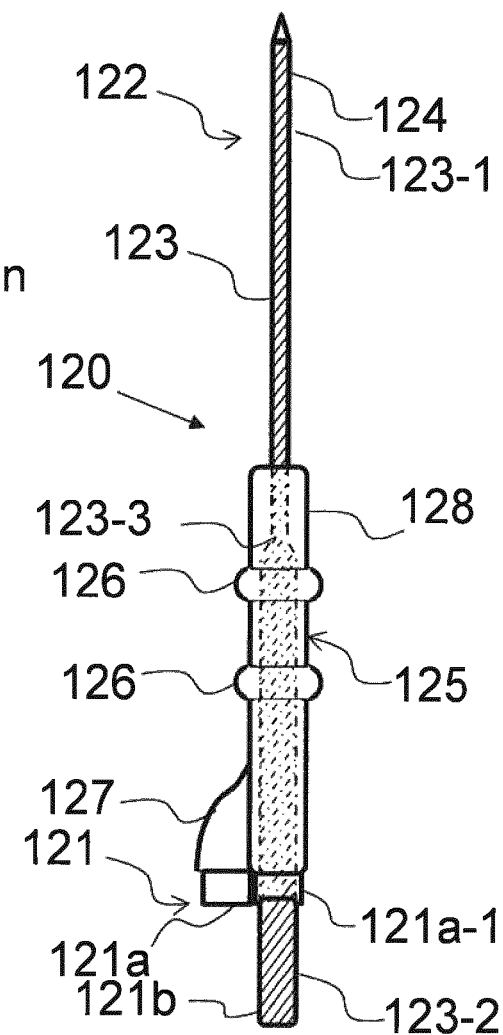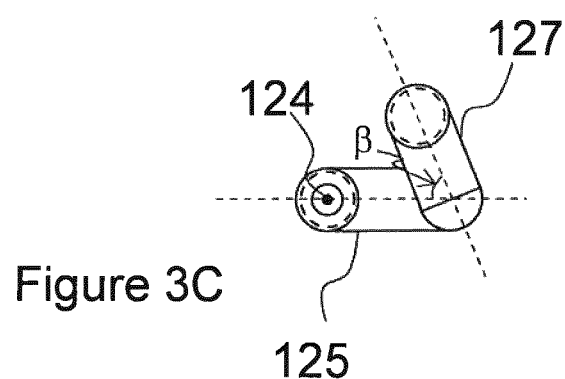
Figure 3A
Figure 3B
Figure 3C

|    | B1 | B2 | B3 | B4 |
|----|----|----|----|----|
| B1 |    | B1-B2 | B1-B3 | B1-B4 |
| B2 | B2-B1 |    | B2-B3 | B2-B4 |
| B3 | B3-B1 | B3-B2 |    | B3-B4 |
| B4 | B4-B1 | B4-B2 | B4-B3 |    |

|     |                  | 1st & 2nd V | Electrode d cm | E V/cm |
|-----|------------------|-------------|----------------|--------|
| R1d | Positive pulses  | 1131-0      | 1.13           | 1000   |
| R1s | Positive pulses  | 800-0       | 0.8            | 1000   |
| R2d | Reversed Pulses  | 0-1131      | 1.13           | -1000  |
| R2s | Reversed Pulses  | 0-800       | 0.8            | -1000  |

ELECTRODE DEVICE AND A NEEDLE ELECTRODE FOR USE IN DELIVERY OF ELECTRICAL PULSES TO A DESIRED TISSUE OF A MAMMAL

This application is a National Stage Application of International Application No. PCT/EP2018/070440, filed Jul. 27, 2018, which claims benefit of Ser. No. 1750965-4, filed Jul. 28, 2017 in Sweden and which application(s) are incorporated herein by reference. To the extent appropriate, a claim of priority is made to each of the above disclosed applications.

TECHNICAL FIELD

Embodiments herein relate to an electrode device, a needle electrode, and to methods therein. Especially, embodiments herein relate to the delivery of electrical pulses to a desired tissue of a mammal.

BACKGROUND

Pulsed electric fields applied to biological cells and tissues create transverse channels or pores in the cell membrane, a phenomenon called electro-permeabilization or electroporation. The explanation to pore formation is the reorganization of interfacial water in structures of the lipid bilayer membranes due to the pulsed applied electric fields.

Electroporation increases the probability for the migration of hydrophilic molecules through the cell membranes. Thus, molecules outside the cells move into the cytoplasm, and out of the cytoplasm migrate intracellular antigenic molecules to the extracellular space. The rate of resealing the membranes and recovery of the cells depend on the strength of applied voltage, and the number and length of the applied electric pulses.

Most electroporation protocols for experimental, clinical, and biotechnological applications use pulses, e.g. direct current (DC) pulses, of about 1000 V/cm, with durations of at least 100 µs. But membrane permeabilization also occurs with shorter pulses with pulse-lengths, in the range of 100 ns, however, at much higher electric field-strength.

The concept of electro-permeabilization is employed in tumour treatment by increasing the permeability of tumour cells, and thus to enhance the access of administered cytotoxic agents to solid tumours. Generally, a low dose of bleomycin, a highly toxic antibiotic agent that normally doesn't penetrate the tumour cell membrane, is administered either intravenously (15000-25000 International Units (IU)), or directly to the tumours (260-1000 IU/cm$^3$) before electric pulses are applied to them. However, a combination of intravenous and direct administration of the agent may be applied. By applying the electric pulses, the therapeutic effect of the chemotherapy can be enhanced.

This procedure applied clinically is usually called Electro-Chemo-Therapy (ECT), and use a pulse-train of 8 rectangular pulses delivered at 5 kHz with a nominal electric field strength of about 1000 V/cm (that means a voltage of 1000 V applied between pin electrodes with distance of about 4-12 mm, e.g. 8-10 mm), with a duration of 100 µs for each pulse. In an example protocol, totally 96 electric pulses may be delivered over a number (e.g. 12) of pairs of electrodes in the applicator. The general hypothesis is that the efficacy of ECT is due to the applied voltage and the distance between the electrodes. The absorbed power per pulse is estimated to about 500 J/kg and the current about 16 A. This seems, however, to be too detrimental to tissues in head and neck treatments. The use of too high electric field-strength and current cause inflammatory response and immune suppression that limit the infiltration of killer T-cells to the treated tumour.

WO9952589A1 discloses an apparatus comprising a voltage generator for generating brief voltage pulses for the impression of voltage on electrodes included in the apparatus, and a measurement unit which is coupled to the electrodes. The electrodes are designed to be secured at or inserted in a tissue in a restricted region of a human or an animal in order to form electric fields in the tissue between the electrodes. The measurement unit is disposed to determine the impedance between the electrodes which is substantially determined by the electric properties of the tissue which is located between the electrodes. A registration and calculator device forms a control unit which, based on the impedance determined by the measurement unit, controls the output voltage of the voltage generator such that the electric field which is formed in the tissue always has a predetermined value. The treatment with the electric field realizes a perforation of cell membranes in the tissue which thereby permits the passage of substances fed to the body, e.g. cytostatic or genetic material.

US 2008/0091135 A1 discloses an electroporation device including a replaceable skin electrode disk which can be removable mounted in a handle assembly. The electrode disk has a plurality of needle skin electrodes mounted on a support structure in a spatial arrangement for penetrating the selected tissue.

A drawback with previously known devices is that it is difficult to adapt the distance between the electrodes to the treatment volume of the mammal.

SUMMARY

An aim of some embodiments disclosed herein is to overcome or mitigate at least some of the drawbacks with the prior art.

According to an aspect of embodiments herein, the object is achieved by an electrode device for use in delivery of electrical pulses to a desired tissue of a mammal.

The electrode device comprises a handle portion comprising a first electrode connection and a second electrode connection.

Further, the electrode device comprises a first needle electrode comprising a first attachment end and a second needle electrode comprising a second attachment end, wherein the first and second attachment ends are configured for releasable attachment to the first electrode connection and the second electrode connection, respectively.

Furthermore, each one of the first and second electrode connections is configured with an inner electrode position and an outer electrode position. The inner and outer electrode positions are electrically conducting.

Yet further, each one of the first and second attachment ends of the electrodes is configured with an insulating part configured to electrically insulate one out of the inner electrode position and the outer electrode position when located therein, and with an electrically conducting part configured to conduct current supplied to the other one out of the inner electrode position or the outer electrode position when located therein.

According to another aspect of embodiments herein, the object is achieved by a needle electrode for use in an electrode device for delivery of electrical pulses to a desired tissue of a mammal.

The needle electrode comprises an attachment end for releasable attachment to an electrode connection of an electrode device.

Further, the attachment end is configured with an insulating part configured to electrically insulate one out of an electrically conducting inner electrode position and an electrically conducting outer electrode position of a first electrode connection when located therein.

Furthermore, the attachment end is configured with an electrically conducting part configured to conduct current supplied to the other one out of the inner electrode position and the outer electrode position when located therein.

Since each one of the first and second electrode connections is configured with the electrically conducting inner electrode position and the electrically conducting outer electrode position, and since each one of the first and second attachment ends of the respective needle electrode is configured with the insulating part configured to electrically insulate one out of the inner electrode position and the outer electrode position when located therein, and with the electrically conducting part configured to conduct current supplied to the other one out of the inner electrode position or the outer electrode position when located therein, the position of the electrically conducting part of the respective needle electrode is able to be varied between the inner electrode position and the outer electrode position.

An advantage with some embodiments disclosed herein is that a distance between the two electrically conducting parts, i.e. between the electrically conducting part of the first needle electrode and the electrically conducting part of the second needle electrode, is able to be easily varied, whereby a treatment area and/or a treatment volume in the mammal, e.g. a patient, easily may be varied.

BRIEF DESCRIPTION OF DRAWINGS

Examples of embodiments herein will be described in more detail with reference to attached drawings in which:

FIG. 3A schematically illustrates embodiments of a needle electrode;

FIG. 3B schematically illustrates embodiments of a needle electrode rotated 90 degrees as compared to the needle electrode of FIG. 3A;

FIG. 3C schematically illustrates a cross-section of embodiments of a needle electrode taken along the line A-A in FIG. 3A;

Alternatively, an excitation to achieve a nominal field strength V/d=1000 V/cm, is to have electrode pair (x;y) with x=+566;y=−566 V at the diagonal excitation and x=+400; y=−400 V along the sides in the first pulse and revered x=−566-;y=+566 V and x=−400;y=+400 V in the second pulse.

DETAILED DESCRIPTION

Clinical applications of Dynamic Electroporation Enhanced Chemotherapy (DEECT™) require an electrode device that easily is able to handle treatment of tumours of different size, e.g. of different area and/or volume. The electrode device described herein is able to vary the position of one or more electrically conducting parts of one or more needle electrodes in order to change the treatment area and/or volume. Further, in the treatment of tumours with an extension that is larger than the area covered by the electrode device, the electrode device may be moved stepwise from the periphery to the centre in a pattern that covers the tumour from the periphery to the centre.

In this disclosure the term electrode device will be used. However, sometimes reference is made to an applicator and such a reference should be understood to refer to the electrode device. Thus, the terms electrode device and applicator are sometimes in this disclosure used interchangeably.

An object addressed by embodiments herein is how to improve performance of an electrode device and to provide an improved needle electrode.

In the following, embodiments herein are illustrated by exemplary embodiments. It should be noted that these embodiments are not mutually exclusive. Components from one embodiment may be tacitly assumed to be present in another embodiment and it will be obvious to a person skilled in the art how those components may be used in the other exemplary embodiments.

It should furthermore be noted that, to anyone skilled in the art, there are several realizations of the embodiments below with principally equivalent functionality.

Figure 1:
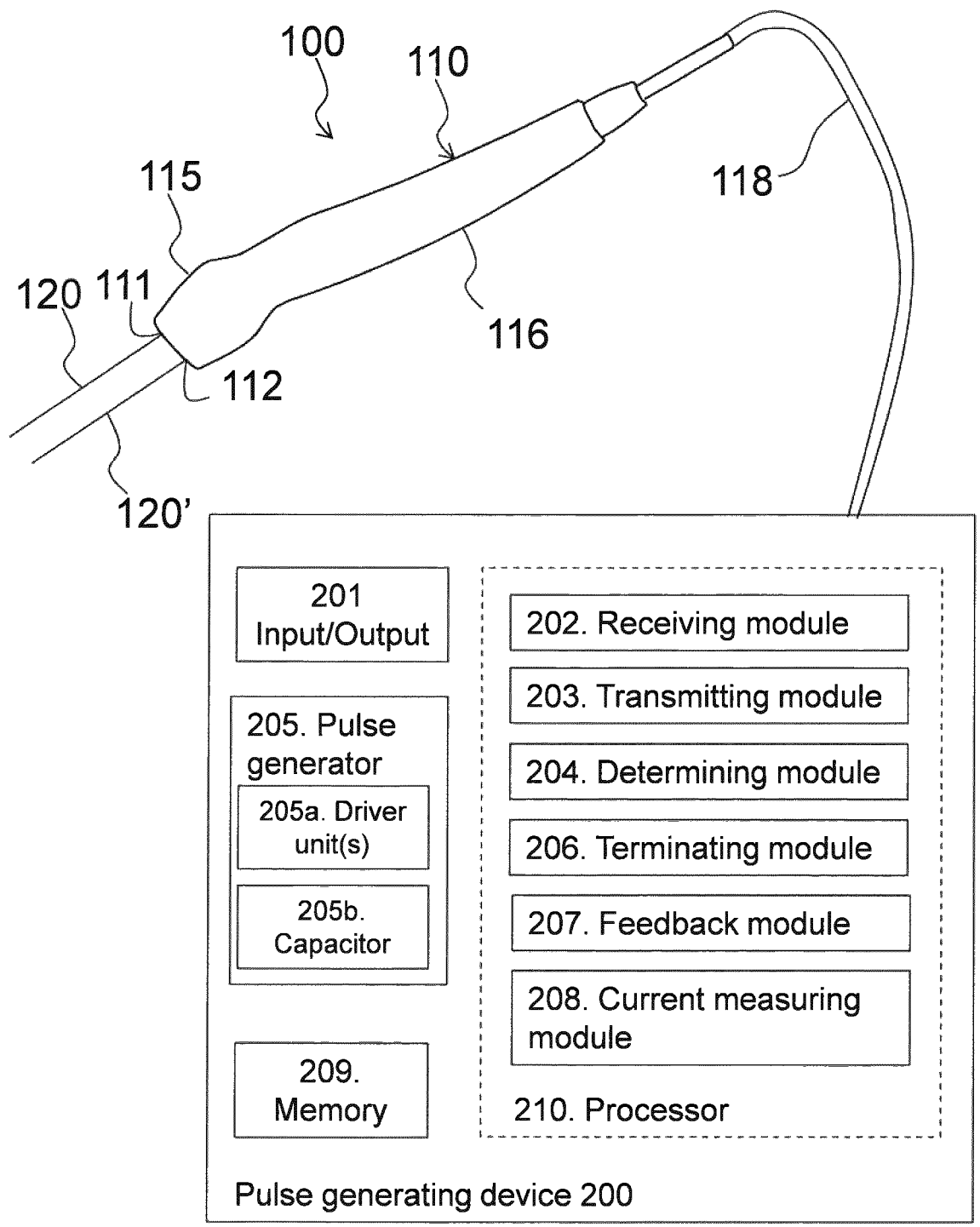
FIG. 1 schematically illustrates embodiments of an electrode device.

FIG. 1 schematically illustrates embodiments of an electrode device 100 for use in delivery of electrical pulses to a desired tissue of a mammal.

The electrode device 100 comprises a handle portion 110 comprising a first electrode connection 111 and a second electrode connection 112. The first and second electrode connections 111, 112 are each a connection for a needle electrode. The needle electrode will be described in more detail below. Thus, by means of the first and second electrode connections 111, 112 two needle electrodes may be attached, e.g. releasably attached, to the handle portion 110.

Figures 4, 5A:
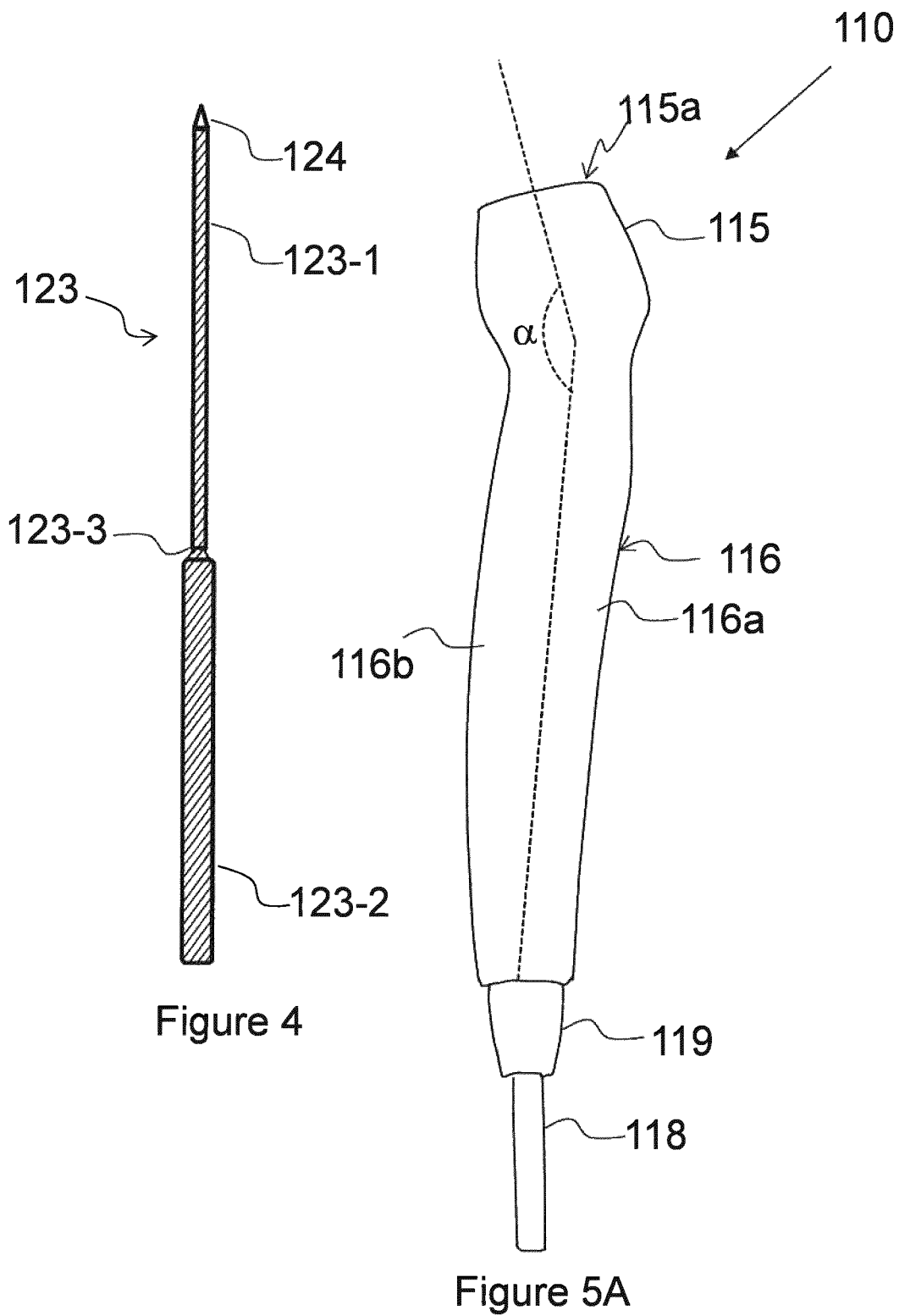
FIG. 4 schematically illustrates embodiments of an electrode.
FIG. 5A schematically illustrates embodiments of a handle portion.

The handle portion 110 may comprise a head portion 115 and a body portion 116 arranged angled in relation to the head portion 115. This is schematically illustrated in FIG. 5A showing embodiments of the handle portion 110. In some embodiments, an angle α between the head portion 115 and the body portion 116 is in the range of 160 to 180 degrees, preferably approximately 170 degrees. In some embodiments, the angle α is 168 degrees. By selecting the angle α in the range of 160 to 180 degrees, preferably approximately 170 degrees, the sight for an operator of the electrode device 100, when using the electrode device 100 for delivery of electric pulses, is improved. Thereby, improving the field of view of the desired tissue during exposure of the electrical pulses. Further, by providing the angle between the head and body portions, the electrode device 100 is more ergonomic to use.

In some embodiments, the handle portion 110 comprises a planar front section 115a. In such embodiments, the first electrode connection 111 and the second electrode connection 112 are arranged in the planar front section 115a. The planar front section 115a may be a part of the head portion 115.

In some embodiments, the handle portion 110 of the electrode device 100 comprises a third electrode connection 113 and a fourth electrode connection 114, cf. FIGS. 2A, 2B, 5A, 5B, 6A and 6B. These may also be arranged in the planar front section 115a. It should be understood that the electrode device 100 comprises at least two electrode connections. Further, it should be understood that the third and fourth electrode connections 113, 114 correspond to the first and second electrode connections 111,112, and thus comprise the corresponding parts and features even if not described in more detail in this disclosure. Thus, by means of the third and fourth electrode connections 113, 114, two needle electrodes may be attached, e.g. releasably attached, to the handle portion 110.

Unused electrode connections may be sealed by an insulating material, e.g. an insulating plug. For example, if the electrode device 100 comprises four electrode connections, but only two needle electrodes are used during treatment, the unused electrode connections may be sealed by means of insulating plugs.

Figure 2A:
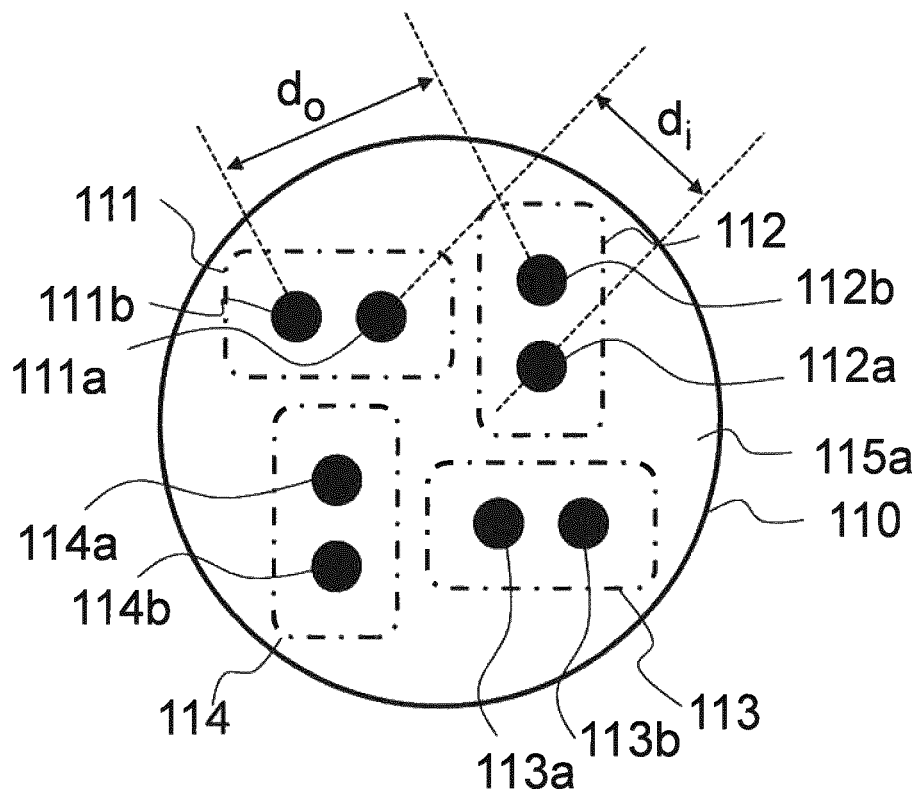
FIG. 2A schematically illustrates a front view of embodiments of an handle portion of an electrode device which handle portion comprises four electrode connections.

Each one of the first and second electrode connections 111,112 is configured with an inner electrode position 111a, 112a and an outer electrode position 111b,112b, wherein the inner and outer electrode positions 111a,112a; 111b,112b are electrically conducting. Thus, each electrode connection 111, 112, comprises two electrically conducting positions for one needle electrode; i.e. one electrically conducting inner electrode position 111a, 112a, and one electrically conducting outer electrode position 111b, 112b. FIG. 2A schematically illustrates a front view of embodiments of an handle portion of an electrode device which handle portion comprises four electrode connections. As schematically illustrated in FIG. 2A, the inner electrode positions 111a, 112a are arranged closer to the centre of the planar front section 115a and the outer electrode positions 111b, 112b are arranged closer to the periphery of the planar front section 115a.

In some embodiments, a distance, e.g. an inner distance, $d_i$ between the inner electrode position 111a of the first electrode connection 111 and the inner electrode position 112a of the second electrode connection 112 is smaller than a distance, e.g. an outer distance, $d_o$ between the outer electrode position 111b of the first electrode connection 111 and the outer electrode position 111b of the second electrode connection 111. This is schematically illustrated in FIG. 2A.

For example, the inner distance $d_i$ may be in the range of about 6-8 mm, preferably about 6 or 8 mm, and the outer distance $d_o$ may be in the range of about 10-12 mm, preferably about 10 or 12 mm.

Further, FIG. 2A schematically illustrates embodiments comprising the third and fourth electrode connection 113, 114 and corresponding electrically conducting inner electrode position 113a,114a and electrically conducting outer electrode position 113b,114b. As schematically illustrated in FIG. 2A, the inner electrode positions 113a, 114a are arranged closer to the centre of the planar front section 115a and the outer electrode positions 113b, 114b are arranged closer to the periphery of the planar front section 115a. Thereby, the inner distance $d_i$ is smaller than the outer distance $d_o$. Consequently, the distance between two electrically conducting parts of two needle electrodes is smaller when the electrically conducting parts are arranged in a respective inner electrode position than when the electrically conducting parts are arranged in a respective outer electrode position.

Figure 5B:
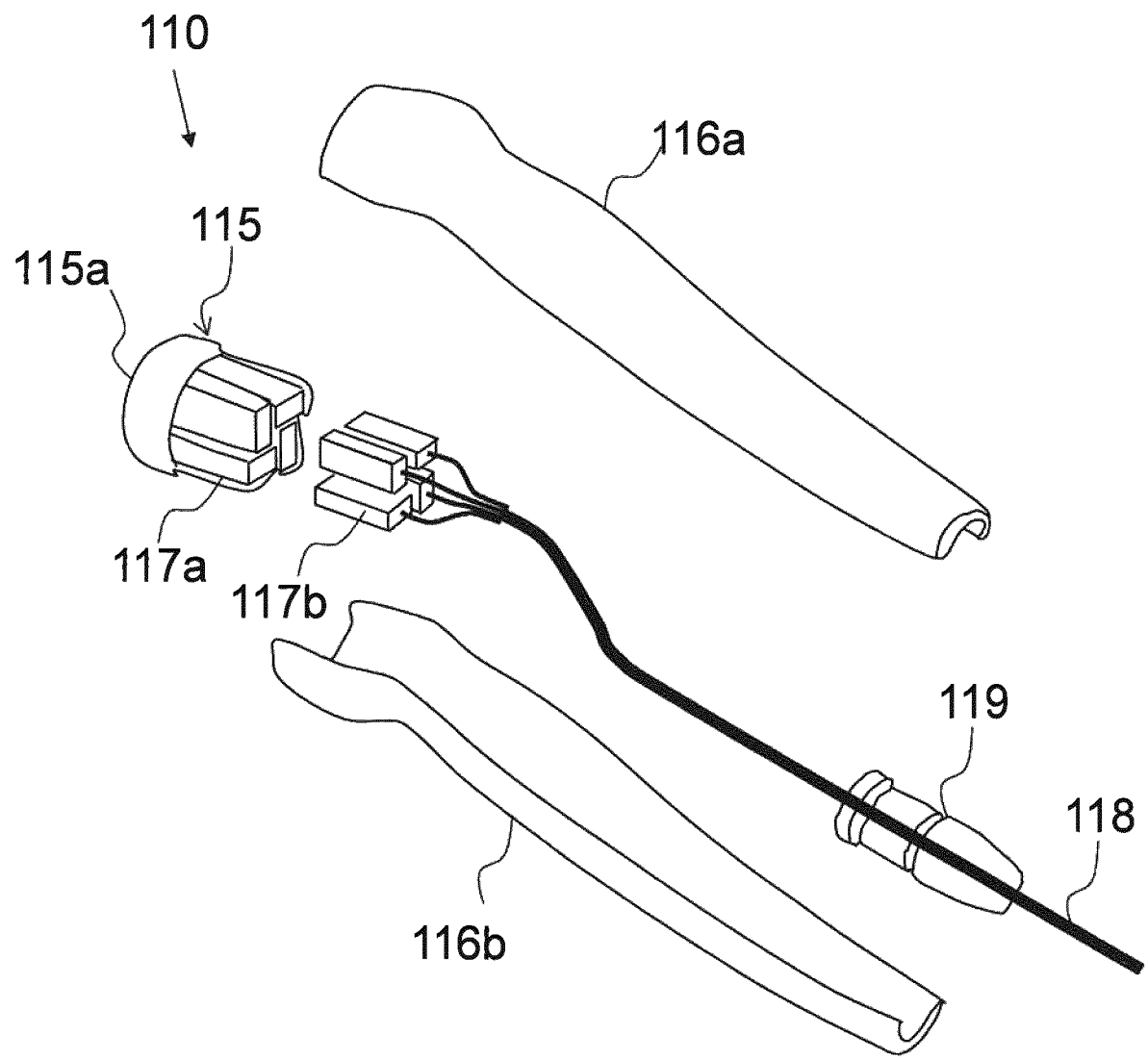
FIG. 5B schematically illustrates an exploded view of embodiments of a handle portion.

FIG. 5B schematically illustrates an exploded view of embodiments of a handle portion 110. As illustrated, the body portion 116 may comprise two cover parts 116a,116b configured to be attached to each other, e.g. by means of snap-fit.

In some embodiments, each one of the first and second electrode connections 111,112 comprises a respective first and second connector 117a,117b configured to connect the respective first and second electrode connections 111,112 to a pulse generating device 200 via electric wiring or cable 118. The pulse generating device 200 will be described in more detail below. One of the first and second connector 117a,117b may be a female connector and the other one of the first and second connector 117a,117b male connector. FIG. 5B further illustrates a cable transition 119 arranged at an end of the handle portion 100 and around the wiring 118.

Further, the electrode device 100 comprises a first needle electrode 120 comprising a first attachment end 121 and a second needle electrode 120' comprising a second attachment end 121', wherein the first and second attachment ends 121,121' are configured for releasable attachment to the first electrode connection 111 and the second electrode connection 112, respectively.

It should be understood that the number of needle electrodes may correspond to the number of electrode connections of the electrode device. Thus, sometimes in this disclosure reference is made to a first needle electrode 120, a second needle electrode 120', a third needle electrode 120", and a fourth needle electrode 120'''. A reference to a needle electrode 120 when no other needle electrode is described should be understood to refer to anyone of the needle electrodes 120,120',120",120'''.

As previously mentioned, the first electrode connection 111 and the second electrode connection 112 may be arranged in the planar front section 115a. In such embodiments, the first and second needle electrodes 120,120' are arranged perpendicular or almost perpendicular to the planar front section 115a when arranged in the respective electrode connection 111,112.

During delivery of the electrical pulses to the desired tissue of the mammal, e.g. the patient, each electrode pair is in a first excitation first excited, by means of the pulse generating device 100, e.g. the pulse generator 105, with positive voltage at one of the electrode, e.g. the first needle electrode 120 and zero voltage at the other needle electrode, e.g. the second needle electrode 120'. Thus, in the first excitation, the electrically conducting part 121b of the first needle electrode 120 will be excited with the positive voltage and the electrically conducting part 121b' of the second needle electrode 120, will be excited with zero voltage. Thereby, a voltage will be applied between the electrically conducting part 121b of the first needle electrode 120 and the electrically conducting part 121b' of the second needle electrode 120 causing treatment of the desired tissue. In a second excitation of each electrode pair the voltage is reversed to zero voltage at one electrode, e.g. the first needle electrode 120, and positive voltage at the other, e.g. the second needle electrode 120', to promote homogeneity of the chemotherapeutic effect in the target volume of the desired tissue. Thus, in the second excitation, the electrically conducting part 121b of the first needle electrode 120 will be excited with zero voltage and the electrically conducting part 121b' of the second needle electrode 120, will be excited with the positive voltage.

In order to promote homogeneous electric field exposure distribution in the treatment volume with 4 electrodes, all 12 possible combinations of positive and negative pulse applications, including diagonal may be applied.

Figure 2B:
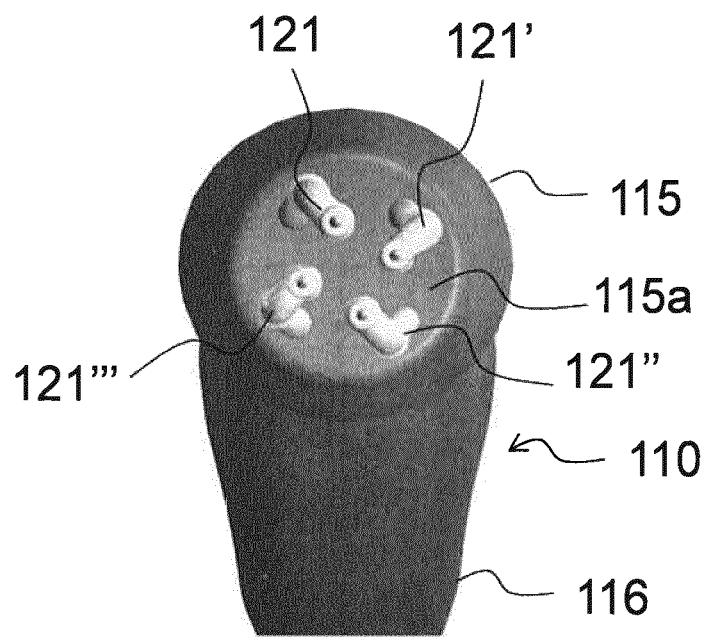
FIG. 2B schematically illustrates a front view of an embodiment of the handle portion comprising four needle electrodes arranged in a respective one electrode connection.

FIG. 2B schematically illustrates a front view of some embodiments of the electrode device 100 comprising four needle electrodes 120,120',120",120'".

FIGS. 3A-3C schematically illustrate some embodiments of the needle electrode 120. Between FIGS. 3A and 3B, the needle electrode 120 has been rotated 90 degrees along its longitudinal axis. FIG. 3C schematically illustrates a cross-section of embodiments of the needle electrode taken along the line A-A in FIG. 3A.

Below embodiments of the first and second needle electrode 120,120' will be described. However it should be understood that described features and parts are equally applicable to some third and fourth needle electrodes 120", 120'". For clarity reasons, in the figures, references are only made to the numbers without the one or more apostrophes indicating whether the respective part belongs to the first, second, third or fourth.

Each one of the first and second attachment ends 121,121' is configured with an insulating part 121a,121'a configured to electrically insulate one of the inner electrode position 111a,112a and the outer electrode position 111b,112b when located therein, and with an electrically conducting part 121b,121'b configured to conduct current supplied to another one of the inner electrode position 111a,112a or the outer electrode 111b,112b when located therein. Thereby, two options exist for the location of the each needle electrode 120,120' at each electrode connection 111,112. In other words, the needle electrode 120 may be arranged in two different ways at each electrode connection 111,112. For example, the electrically conducting part 121b,121b' may either be located in the inner electrode position or the outer electrode position. When the electrically conducting part 121b,121b' is located in the inner electrode position, the corresponding insulting part 121a,121a' is located in the outer electrode position and vice versa.

The insulating part 121a of the attachment end 121 may further be configured to provide a sealed fitting of the insulating part to the inner or outer electrode position of the electrode connection 111,112. A sealing 121a-1 may be provided around the electrically conducting part 121b,121b' of the attachment end in order to provide a sealed fitting of the electrically conducting part to the inner or outer electrode position of the electrode connection 111,112.

As previously described, the distance between the two inner electrode positions 111a,112a is $d_i$ and thus the distance between the centre of two electrically conducting parts 121b,121b' arranged in the inner electrode positions 111a, 112a will be $d_i$. Correspondingly, the distance between the centre of two electrically conducting parts 121b,121b' arranged in the outer electrode positions 111b,112b will be $d_o$.

Each one of the first and second needle electrodes 120, 120' may in an end 122,122' opposite the attachment end 121,121' comprises an electrode tip 124,124' to be arranged at the desired tissue of the mammal. The electrode tip 124,124' may be pointed for easily insertion into the desired tissue.

In some embodiments, each one of the first and second needle electrodes 120,120' comprises a first electrode and a second electrode 123, respectively. FIG. 4 schematically illustrates embodiments of an electrode 123. The first and second electrodes 123 extend in a longitudinal direction through an insulating portion 125 of the respective one of the first and second needle electrodes 120,120'.

The respective first and second electrode tip 124 may be arranged at a respective end of a respective first section 123-1 of the electrode 123. A respective second section 123-2 of the electrode 123,123' opposite the first section 123-1 may comprise the electrically conducting part 121b.

In some embodiments, the electrically conducting part 121b is an integrated part of the electrode 123 and the insulating part 121a is an integrated part of the insulating portion 125. In such embodiments, the needle electrode 120 may be referred to as comprising two parts, e.g. the electrode 123 and the insulating portion 125.

As previously described, in some embodiments the handle portion 110 comprises the third and the fourth electrode connection 113,114 with a respective electrically conducting inner electrode position 113a,114a and a respective electrically conducting outer electrode position 113b,114b. In such embodiments, the electrode device 100 may further comprise the third needle electrode 120" comprising a third attachment end 121" and a fourth needle electrode 120'" comprising a fourth attachment end 121'". Further, the respective attachment end 121",121'" may be configured for releasable attachment to the respective third and fourth electrode connection 113,114. Furthermore, the respective attachment end 121",121'" may be configured with a respective insulating part 121a",121a'" configured to electrically insulate the respective inner electrode position 113a,114a or the respective outer electrode position 113b,114b when located therein, and with a respective electrically conducting part 121b",121b'" configured to conduct current supplied to the respective inner electrode position or the respective outer electrode position when located therein.

As previously mentioned, FIG. 3 schematically illustrates embodiments of the needle electrode 120. The needle electrode 120 for use in an electrode device 100 for delivery of electrical pulses to a desired tissue of a mammal or patient comprises the attachment end 121 for releasable attachment to the electrode connection 111,112,113,114 of the electrode device 100. The attachment end 121 is configured with the insulating part 121a configured to electrically insulate one of the inner electrode position 111a,112a,113a,114a and the outer electrode position 111b,112b,113b,114b of the electrode connection 111,112,113,114 when located therein, and with an electrically conducting part 121b configured to conduct current supplied to another one of the inner electrode position 111a,112a,113a,114a and the outer electrode position 111b,112b,113b,114b when located therein.

As also mentioned above and in some embodiments, the needle electrode 120 comprises, in the end 122 opposite the attachment end 121, the electrode tip 124 to be arranged at the desired tissue of the mammal, e.g. the patient.

Further, as also mentioned previously, the needle electrode 120 comprises the insulating portion 125 and the elongated electrode 123 extending in the longitudinal direction through the insulating portion 125.

In some embodiments, the electrode tip 124 is arranged at an end of the first section 123-1 of the electrode 123, and the second section 123-2 of the electrode 123, opposite the first part 123-1 and at least partly extended out from the insulating portion 125, may comprise the electrically conducting part 121b. The electrode 123 may further comprise a third section 123-3 at which the first and second sections 123-1, 123-2 are connected. The electrode 123 may have a diameter in the first section 123-1 that is smaller than a diameter of the electrode 123 in the second section 123-2.

In some embodiments, the first part 123-1 of the electrode 123 comprises a first conductive alloy providing increased stiffness as compared to a stiffness of the second part 123-2, and wherein the second part 123-2 of the electrode 123 comprises a second conductive alloy providing electrical contact with the electrode connection 111,112,113,114 of the electrode device 100.

The insulating part 121a and the conducting part 121b may be arranged parallel in a longitudinal direction of the needle electrode 120. Further, in some embodiments, the insulating portion 125 may, in a twisted section 127 comprising the insulating part 121a, be twisted to arrange the insulating part 121a at an angle β relative the conducting part 121b. This is schematically illustrated in FIG. 3C. For example, the angle β may be in the range of 20 to 50 degrees, and preferably in the range of 30 to 40 degrees. In some embodiments the angle β is approximately 36 degrees.

The insulating portion 125 may consist of an insulating material and may comprise one or more protrusions 126 arranged at its envelope surface. The one or more protrusions 126 may form a grip of the needle electrode 120. Further, the sealing 121a-1 may form a part of the insulating portion 125.

An untwisted section 128 of the insulating portion 125 may comprise the one or more protrusions 126.

Figure 6A:
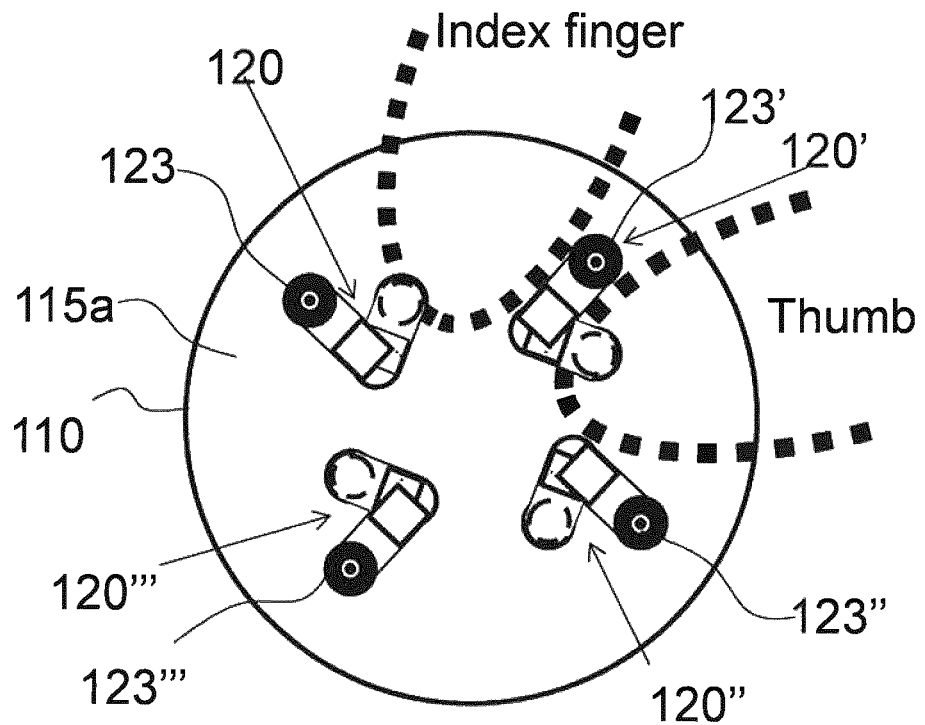
FIG. 6A schematically illustrates an example wherein a respective electrode of four needle electrodes are located in a respective outer electrode position of the handle portion.
Figure 6B:
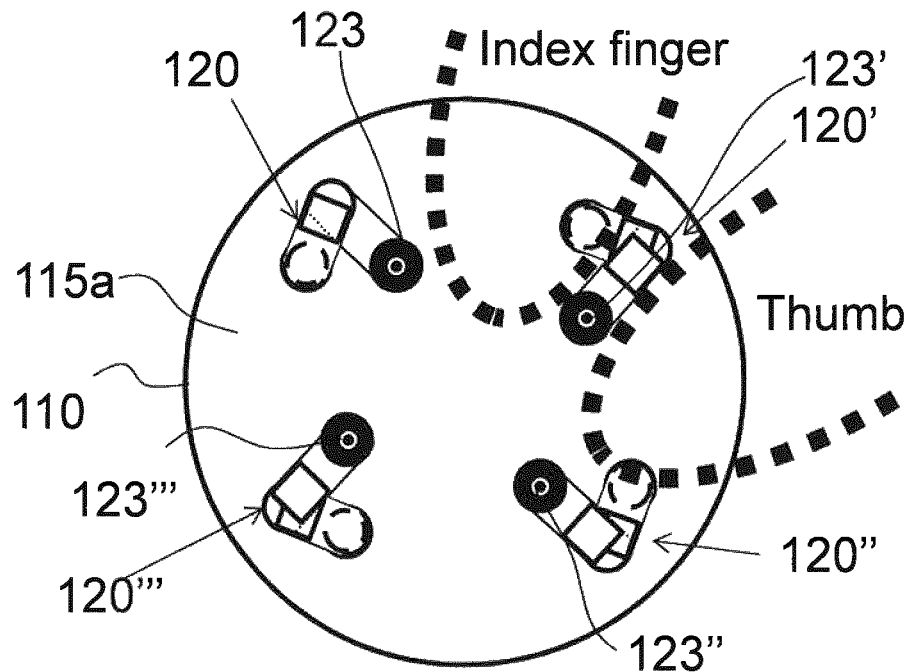
FIG. 6B schematically illustrates an example wherein a respective electrode of four needle electrodes are located in a respective inner electrode position of the handle portion.

FIG. 6A schematically illustrates an example wherein a respective electrode 123,123',123", 123''' of four needle electrodes 120,120',120",120''' are located in a respective outer electrode position of the handle portion. FIG. 6B schematically illustrates an example wherein a respective electrode 123,123',123", 123''' of four needle electrodes 120,120',120",120''' are located in a respective inner electrode position of the handle portion.

Further, FIGS. 6A and 6B schematically illustrate how an index finger and a thumb may grip the insulating portion 125' of the second needle electrode 120'. Especially, the index finger and the thumb may grip the untwisted section 128 of the insulating portion 125'.

As illustrated in FIG. 6A, the twist of the twisted section 127' provides enough space to for the index finger and the thumb to grip the untwisted section 128' while the insulating part 121a' is arranged in the inner electrode position 112a and while the electrically conducting part 121b' is arranged in the outer electrode position 112b.

As illustrated in FIG. 6B, the twist of the twisted section 127' provides enough space to for the index finger and the thumb to grip the untwisted section 128' while the insulating part 121a' is arranged in the outer electrode position 112b and while the electrically conducting part 121b' is arranged in the inner electrode position 112a.

Figure 7:
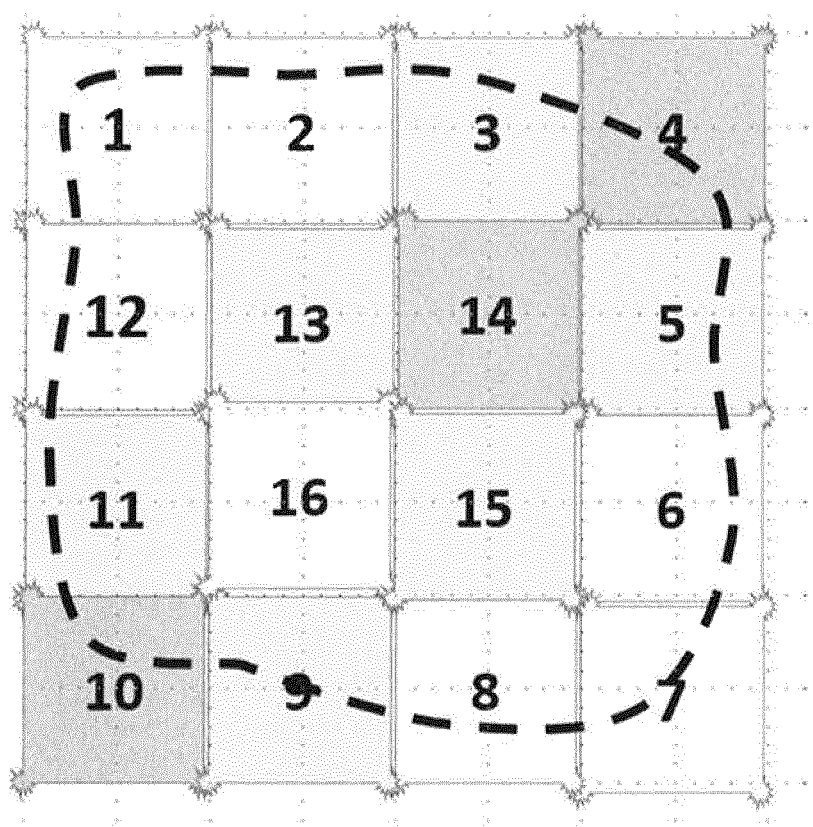
FIG. 7 schematically illustrates how the electrode device may be moved stepwise to cover a certain area.

FIG. 7 schematically illustrates how the electrode device 100 may be moved stepwise to cover a certain area. The dotted line in FIG. 7 schematically illustrates the outlie of the desired tissue and the number 1 to 16 illustrates an example of a stepwise movement of the electrode device from a position 1 to a position 16. The edges of each box schematically illustrates the location of four electrodes used.

Examples of a Pulse Generating Device 200

The pulse generating device 200 may comprise an input/output interface 201, to facilitate communications with a user such as an operator of the pulse generating device 200. The interface may, for example, comprise an output device such as a monitor e.g. a display device, an input device such as a keyboard, keypad, a mouse, or a combined input and output device such as a touch screen. The input and output interface 201 may additionally or alternatively comprise means for wired or wireless communication with another device (not shown).

The pulse generating device 200 may be configured to receive, by means of a receiving module 202 configured to receive, information or data from one or more other devices. The receiving module 202 may be implemented by or arranged in communication with a processor 210 of the pulse generating device 200.

The pulse generating device 200 may be configured to transmit, by means of a transmitting module 203 configured to transmit, information or data to one or more other devices. The transmitting module 203 may be implemented by or arranged in communication with the processor 210 of the pulse generating device 200.

The pulse generating device 200 may be configured to, e.g. by means of a determining module 204 configured to, determine a voltage amplitude of an electrical pulse to be generated between the at least two needle electrodes 120, 120', and to determine a number of consecutive electrical pulses to be generated. The determining module 204 may be implemented by or arranged in communication with the processor 210 of the pulse generating device 200.

The pulse generating device 200 may further be configured to, e.g. by means of the determining module 204, to determine a pulse shape of the electrical pulses to be generated, and/or a pause period e.g. a time period during which the generation of pulses is to be paused and thus during which time period no pulses is to be generated.

The pulse generating device 200 may be configured to, e.g. by means of a pulse generator 205 configured to, generate one or more electrical pulses. The pulse generator 205 may be arranged in communication with the processor 210 of the pulse generating device 200.

The pulse generating device 200, e.g. by means of the pulse generator 205, is arranged in electrical communication with the at least two needle electrodes 120,120' and configured to generate one or more of the determined, e.g. predetermined, number of consecutive electrical pulses such that the generated first electrical pulse has the first voltage amplitude and that the one or more generated consecutive electrical pulses have a respective voltage amplitude consecutively decreasing between consecutively generated electrical pulses. Thereby, an increase in a current value of the one or more generated consecutive electrical pulses above a threshold value is avoided.

In some embodiments, the pulse generating device 200, e.g. by means of the pulse generator 205, is configured to generate the one or more of the determined number of consecutive electrical pulses with a respective voltage amplitude that is decreasing with a pre-set amplitude value between two consecutive electrical pulses, wherein the preset amplitude value is in the range of 400-1200 V.

The pulse generating device 200, e.g. by means of the pulse generator 205, may be configured to generate the one or more of the determined number of consecutive electrical pulses with a respective voltage amplitude that is exponentially decreasing between two consecutive electrical pulses. For example, the respective voltage amplitude may be exponentially decreasing between two generated consecutive electrical pulses as a function of $-f_c t$, wherein $f_c = \sigma/C$, $\sigma$ is the conductivity of the desired tissue, C is the capacitance of a capacitor of the pulse generator 205, and t is the time between the two generated consecutive electrical pulses.

In some embodiments, the pulse generating device 200, e.g. by means of the pulse generator 205, is configured to first excite a first one of the two electrodes 120,120' with a positive voltage and a second one of the two electrodes 201,202 with zero voltage. The pulse generator 205 may then in a second excitation excite the second one of the two electrodes 120,120' with the positive voltage and the first one of the two electrodes with zero voltage. Thereby, an improved homogeneity of the therapeutic effect in the target volume is achieved. It should be that in a third excitation the pulse generator 105 may excite the first one of the two electrodes 120,120' with a positive voltage and the second one of the two electrodes 120,120' with zero voltage, and this may be repeated for every following excitation. It should be understood that each excitation corresponds to one generated pulse.

In some embodiments, the pulse generating device 200, e.g. by means of the pulse generator 205, is configured generate pulses to four needle electrodes positioned in a respective corner of a square of the desired tissue. By such positioning of the electrodes, the treatment volume may be easily changed. In order to promote homogeneous E-field distribution in the treatment volume with four electrodes, all 12 possible combinations of positive and negative pulse applications, including horizontal, vertical and diagonal will be applied such as in the first excitation of each electrode pair the voltage of one of the electrodes, is positive and corresponding electrode is at zero voltage, in a second excitation the voltage at one electrode is reversed to zero, and to positive voltage at the corresponding electrode. This pattern may be executed by the pulse generating device 200 for all electrode combinations to promote homogeneity of the electro-enhanced chemo-therapeutic effect in the target volume.

One or more driver units 205a may be comprised in or connected to the pulse generator 205. Each of the one or more driver units 205a may be configured to generate an electrical pulse between a pair of electrodes 120,120',120", 120'''. Thus, in case of several pairs of electrodes, the pulse generator 205 may comprise a driver unit 205a for each pair of electrodes, and consequently the number of driver units 205a corresponds to the number of pairs of electrodes. However, it should be understood that the number of driver units 205a may be less than or more than the number of electrode pairs.

One or more capacitors 205b may be comprised in or connected to the pulse generator 205. Each one of the one or more capacitors 205b may be charged to a desired voltage value, e.g. the pre-set voltage value, and configured to be discharged to create one or more electrical pulses. For example, the capacitor 205b may be configured to be discharged stepwise to create a pulse The pulse generating device 200 may be configured to, e.g. by means of a terminating module 206 configured to, terminate generation of one or more electrical pulses. The terminating module 206 may be implemented by or arranged in communication with the processor 210 of the pulse generating device 200.

The pulse generating device 200, e.g. by means of the terminating module 206, may be configured to terminate generation of the one or more of the determined number of electrical pulses when a value of a total absorbed energy, caused in the desired tissue by the one or more generated electrical pulses, exceeds a desired threshold value.

In some embodiments, the absorbed energy is a specific absorbed energy, e.g. an absorbed energy value given per kilogram.

The pulse generating device 200, e.g. by means of the terminating module 206, may further be configured to terminate generation of the one or more of the determined number of electrical pulses when one of the respective current values of the generated electrical pulses is outside the desired current interval.

The pulse generating device 200 is configured to, e.g. by means of a feedback module 207 configured to, give feedback relating to one or more generated electrical pulses. The feedback module 207 may be implemented by or arranged in communication with the processor 210 of the pulse generating device 200.

In some embodiments, the pulse generating device 200, e.g. by means of the feedback module 207, is configured to determine a respective absorbed energy of each one of the one or more generated electrical pulses and to send information relating to the determined respective absorbed energy, and possibly the respective generated electrical pulse, to the terminating module 206.

The pulse generating device 200 may be configured to, e.g. by means of a current measuring module 208 configured to, measure the current of a pulse, e.g. the current of a generated pulse. The current measuring module 208 may be implemented by or arranged in communication with the processor 210 of the pulse generating device 200.

The pulse generating device 200 may also comprise or be connected to means for storing data. In some embodiments, the pulse generating device 200 may further comprise or be connected to a memory 209 configured to store the data relating to the delivery of electrical pulses to the desired tissue of the mammal. The data may be processed or non-processed data and/or information relating thereto. The memory 209 may comprise one or more memory units. Further, the memory 209 may be a computer data storage or a semiconductor memory such as a computer memory, a read-only memory, a volatile memory or a non-volatile memory. The memory 209 is arranged to be used to store obtained information, data, configurations, and applications to perform the methods herein when being executed in the pulse generating device 200.

Embodiments herein for delivery of electrical pulses to the desired tissue of the mammal may be implemented through one or more processors, such as the processor 210 in the arrangement depicted in FIG. 1, together with computer program code for performing the functions and/or method actions of embodiments herein. The program code mentioned above may also be provided as a computer program product, for instance in the form of a data carrier carrying computer program code for performing the embodiments herein when being loaded into the pulse generating device 200. One such carrier may be in the form of an electronic signal, an optical signal, a radio signal or a computer readable storage medium. The computer readable storage medium may be a CD ROM disc, SIM card or a memory stick.

The computer program code may furthermore be provided as program code stored on a server and downloaded to the pulse generating device 200.

Those skilled in the art will also appreciate that the input/output interface 201, the receiving module 202, the transmitting module 203, the determining module 204, the pulse generator 205, the terminating module 206, the feedback module 207, and the current measuring module 208 above may refer to a combination of analogue and digital circuits, and/or one or more processors configured with software and/or firmware, e.g. stored in the memory 209, that when executed by the one or more processors such as the processors in the pulse generating device 200 perform as described above. One or more of these processors, as well as the other digital hardware, may be included in a single Application-Specific Integrated Circuitry (ASIC), or several processors and various digital hardware may be distributed among several separate components, whether individually packaged or assembled into a System-on-a-Chip (SoC).

Electrode Material

Different electrochemical processes occur at an anode, e.g. the first electrode 120, and a cathode, e.g. the second electrode 120'. It should be understood that the anode is an electrode from which negative charged electrons exit and positively charged current enters, and the cathode is an electrode from which positively charged current enters and negatively charged electrons exit. If hydrogen gas is present it forms at the cathode positive metal ions that are deposited. Chlorine and oxygen gas is released at the anode, as well as ions extracted from the metallic electrode. Iron-ions stimulate the activity of Bleomycin and initiate the so-called Haber-Weiss reaction to form aggressive .OH radicals. Thus, the chemical environment at the cathode is most toxic to the tissue. These processes increase with the amount of charge displacement Q.

The charge displacement Q (As/m$^2$), is defined by the equation below, and is a parameter to consider when estimating the efficiency of electroporation in vivo.

Charge displacement $Q$ for a single pulse (As/m$^2$),
$Q = J \cdot t_p$ [As·m$^{-2}$]

Charge displacement for $N$ pulses $Q = \Sigma_{n=1}^{N} \sigma_n \cdot E \cdot t_p$ (As/m$^2$), Wherein $\sigma$=tissue conductivity [S·m$^{-1}$]

$\sigma_n$=tissue conductivity during each individual pulse n [S·m$^{-1}$]

J=current density [A·m$^{-2}$]

E=applied electric field strength [V·m$^{-1}$]

$t_p$=pulselength [s]

N=total number of pulses

Faraday's laws may be summarized by $$N = \frac{g}{M} \cdot A = \frac{Q}{F \cdot z} \cdot A$$

Wherein:

N is the number of molecules released at an electrode g is the mass of the substance in gram liberated at an electrode in grams M is the molar mass of the substance in grams per mol A is the Avogadro's number 6.023·10$^{23}$ that is the number of molecules, or atoms in one mole (g/M) of substance (defined as its molecular weight in grams)

Q is the total electric charge passed through the substance in coulombs

F=96485 As·mol$^{-1}$ is the Faraday constant z is the valence number of ions of the substance (electrons transferred per ion).

At a tissue conductivity of 0.1 S·m$^{-1}$, field-strength 1000 V·cm$^{-1}$, pulse-length 0.1 ms, about 3,12·10$^{15}$ molecules per cm$^3$ is generated for each pulse at the electrodes, which corresponds to concentrations in the range of 5 nano-molar.

Dynamic Electro Enhanced Chemotherapy (D-EECT)

In Dynamic Electro Enhanced Chemotherapy (D-EECT) a pulse-train of electrical pulses of gradually decreasing voltage, e.g. pseudo exponentially decreasing voltage, is applied and the electrical current in each pulse is controlled to not exceed an upper current threshold value, e.g. a pre-set current threshold value in the order of 6-14 A, e.g. in the order of 6-10 A. The reason for controlling the electrical current of each pulse is that the magnitude of the electrical current generated in each pulse influence the clinical outcome of the treatment and should therefore be controlled.

The electrical current in the pulse depends on the conductivity of the organ or tissue to be treated. Further, the conductivity varies widely between various tissues and organs. For example, conductivity values of in vivo human tissues vary between 0.02-1.5 S/m at a low frequency <1 kHz. In tissue phantoms (saline, film), examined by Magnetic Resonance Imaging (MRI) combined with electrical impedance tomography, the conductivity is about 0.09 S/m. Further, in prostate tissue the electrical conductivity increases from 0.3 to 0.9 S/m due to exposure of high voltage pulses, e.g. pulses of 1100 V/cm.

The D-EECT promote homogeneous treatment efficiency in the target volume by reverting the polarity at every second pulse of the same electrode pair.

Figure 8:
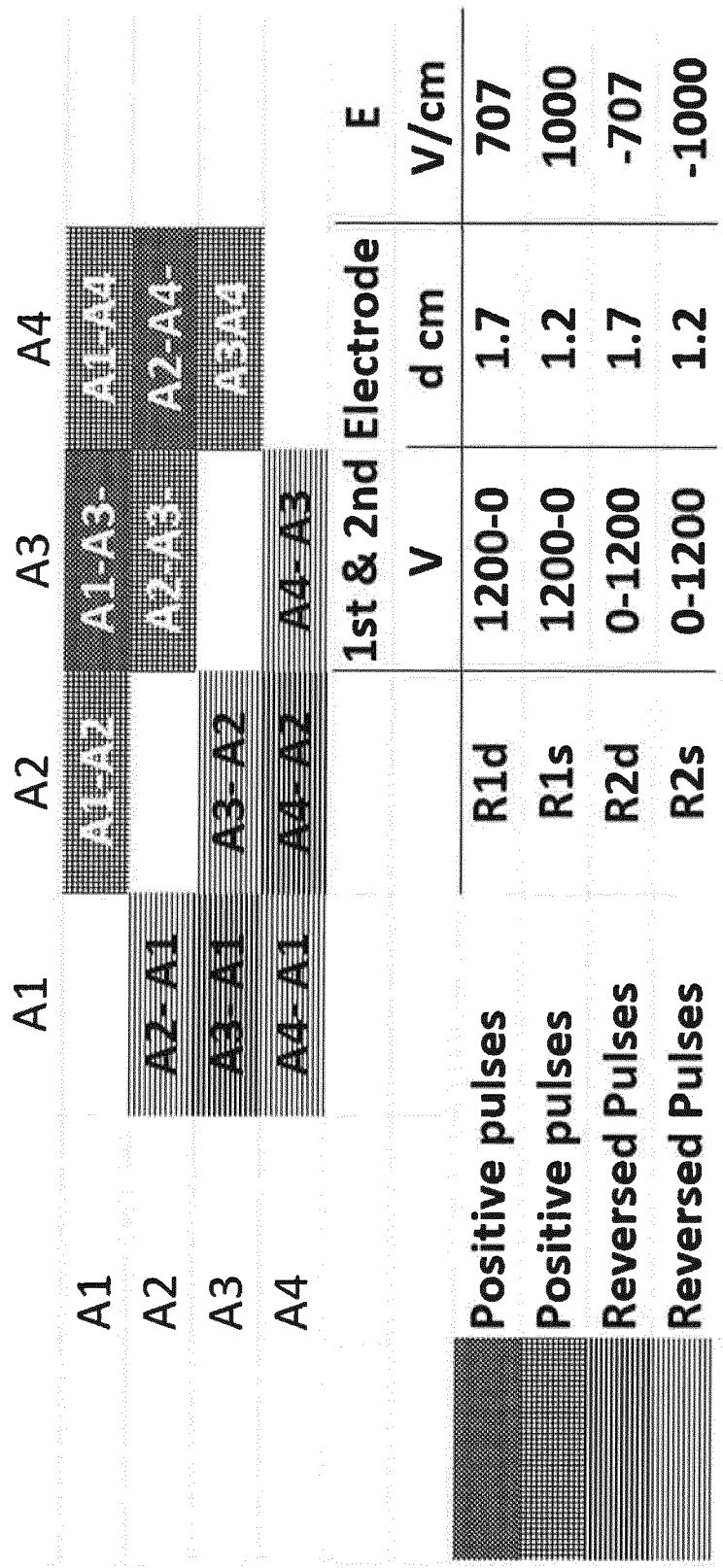
FIG. 8 schematically shows a matrix of the possible electrode pair combinations in case A (12 mm between the electrodes of an electrode pair), and the excitation with 1200-0 V at the outer electrode position A1 in the first pulse and 0-1200V and at outer electrode position A4 in the second pulse, and FIG. 9 schematically shows a matrix of the possible electrode pair (x;y) combinations in case B (8 mm between the electrodes of an electrode pair), and the excitation to achieve a nominal field strength V/d=1000 V/cm, with x=1131;y=0 V at the diagonal excitation and x=800-;y=0 V along the sides in the first pulse and revered x=0-;y=1131 V and x=0;y=800 V in the second pulse.

With all 4 electrodes 120,120',120",120''' positioned in their respective outer electrode position 111b,112b,113b, 114b the following electrode pair excitations may be performed with the maximum applied voltage of 1200 V. This is also illustrated in FIG. 8, wherein the outer electrode positions are referred to as A1, A2, A3, and A4. FIG. 8 shows a matrix of the possible electrode pair combinations in case A (12 mm between the electrodes of an electrode pair), and the excitation with 1200-0 V at the outer electrode position A1 in the first pulse and 0-1200V and at outer electrode position A4 in the second pulse.

The electrode pair excitation may comprise a first pulse sequence with:

a first pulse with the outer electrode position A1 as positive voltage, and the outer electrode positions A2, A3, and A4 as zero voltage;

a second pulse with the outer electrode position A2 as positive voltage, and the outer electrode positions A3, and A4 as zero voltage; and a third pulse with the outer electrode position A3 as positive voltage and the outer electrode position A4 as zero voltage.

Further, the electrode pair excitation may comprise a second pulse sequence with:

a first pulse with the outer electrode position A4 as positive voltage and the with the outer electrode positions A1, A2, and A3 as zero voltage;

a second pulse with the outer electrode position A3 as positive voltage and the outer electrode positions A1, and A2 as zero voltage; and a third pulse with the outer electrode position A2 as positive voltage (red) and the outer electrode position A1 as zero voltage.

With all 4 electrodes 120,120',120",120''' positioned in their respective inner electrode position 111a,112a,113a, 114a the following electrode pair excitations may be performed with the maximum applied voltage of 1200 V. This is also illustrated in FIG. 9, wherein the inner electrode positions are referred to as B1, B2, B3, and B4. FIG. 9 shows a matrix of the possible electrode pair combinations in case B (8 mm between the electrodes of an electrode pair), and the excitation to achieve a nominal field strength V/d=1000 V/cm, with 1131-0 V at the diagonal excitation and 800-0 V along the sides in the first pulse and reversed 0-1131 V and 0-800 V in the second pulse.

In other words, FIG. 9 schematically shows a matrix of the possible electrode pair (x;y) combinations in case B (8 mm between the electrodes of an electrode pair), and the excitation to achieve a nominal field strength V/d=1000 V/cm, with x=1131;y=0 V at the diagonal excitation and x=800;y=0 V along the sides in the first pulse and reversed x=0-;y=1131 V and x=0;y=800 V in the second pulse.

The electrode pair excitation may comprise a first pulse sequence with:

a first pulse with the inner electrode position B1 as positive voltage, and a the inner electrode positions B2, B3, and B4 as zero voltage;

a second pulse with the inner electrode position B2 as positive voltage, and the inner electrode positions B3, and B4 as zero voltage; and a third pulse with the inner electrode position B3 as positive voltage, and the inner electrode position B4 as zero voltage.

Further, the electrode pair excitation may comprise a second pulse sequence with:

a first pulse with the inner electrode position B4 as positive voltage, and the inner electrode positions B1, B2, and B3 as zero voltage;

a second pulse with the inner electrode position B3 as positive voltage, and the inner electrode positions B1, and B2 as zero voltage; and a third pulse with the inner electrode position B2 as positive voltage, and the inner electrode position B1 as zero voltage.

The resistivity values R1d, R1s, R2d, and R2s are saved and stored in a data base, e.g. in the memory 209.

Alternatively, an excitation to achieve a nominal field strength V/d=1000 V/cm, is to have electrode pair (x;y) with x=+566;y=−566 V at the diagonal excitation and x=+400; y=−400 V along the sides in the first pulse and revered x=−566-;y=+566 V and x=−400;y=+400 V in the second pulse.

When the word "comprise" or "comprising" is used in this disclosure it shall be interpreted as non-limiting, i.e. meaning "consist at least of".

Modifications and other variants of the described embodiment(s) will come to mind to one skilled in the art having the benefit of teachings presented in the foregoing descriptions and the associated drawings. Therefore, it is to be understood that the embodiment(s) herein is/are not be limited to the specific examples disclosed and that modifications and other variants are intended to be included within the scope of this disclosure. Although specific terms may be employed herein, they are used in a generic and descriptive sense only and not for purposes of limitation.

The invention claimed is:

1. An electrode device for use in delivery of electrical pulses to a desired tissue of a mammal, wherein the electrode device comprises:

a handle portion comprising a first electrode connection and a second electrode connection, a first needle electrode comprising a first attachment end and a second needle electrode comprising a second attachment end, wherein the first and second attachment ends are configured for releasable attachment to the first electrode connection and the second electrode connection, respectively; wherein:

each one of the first and second electrode connections is configured with an inner electrode position and an outer electrode position, wherein the inner and outer electrode positions are electrically conducting; and in that each one of the first and second attachment ends is configured with an insulating part configured to electrically insulate one out of the inner electrode position and the outer electrode position when located therein, and configured with an electrically conducting part configured to conduct current supplied to the other one out of the inner electrode position or the outer electrode position when located therein.

2. The electrode device of claim 1, wherein a distance $d_i$ between the inner electrode position of the first electrode connection and the inner electrode position of the second electrode connection is smaller than a distance $d_o$ between the outer electrode position of the first electrode connection and the outer electrode position of the second electrode connection.

3. The electrode device of claim 1, wherein each one of the first and second needle electrodes in an end opposite the attachment end comprises an electrode tip to be arranged at the desired tissue of the mammal.

4. The electrode device of claim 3, wherein each one of the first and second needle electrodes comprises a first electrode and a second electrode, respectively, extending in a longitudinal direction through a respective insulating portion of the respective one of the first and second needle electrodes, wherein the respective first and second electrode tip is arranged at a respective end of a respective first section of the electrode and wherein a respective second section of the electrode opposite the first section comprises the electrically conducting part.

5. The electrode device of claim 1, wherein the handle portion comprises a head portion and a body portion arranged angled in relation to the head portion, wherein an angle a between the head portion and the body portion is in the range of 10 to 30 degrees.

6. The electrode device of claim 1, wherein the handle portion comprises a planar front section, and wherein the first electrode connection and the second electrode connection are arranged in the planar front section such that the first and second needle electrodes when arranged in the respective electrode connection are arranged perpendicular to the planar front section.

7. The electrode device according to claim 1, wherein each one of the first and second electrode connections comprises a respective first and second connector configured to connect the respective first and second electrode connections to a pulse generating device via electric wiring.

8. The electrode device of claim 1, wherein the handle portion further comprises a third and a fourth electrode connection with a respective electrically conducting inner electrode position and a respective electrically conducting outer electrode position and wherein the electrode device further comprises:

a third needle electrode comprising a third attachment end and a fourth needle electrode comprising a fourth attachment end, wherein the respective attachment end is configured for releasable attachment to the respective third and fourth electrode connection; and wherein the respective attachment end is configured with a respective insulating part configured to electrically insulate the respective inner electrode position or the respective outer electrode position when located therein, and with a respective electrically conducting part configured to conduct current supplied to the respective inner electrode position or the respective outer electrode position when located therein.

9. The electrode device of claim 1, wherein the first needle electrode and the second needle electrode each comprises an attachment end for releasable attachment to an electrode connection of the electrode device, wherein:

the attachment end is configured with an insulating part configured to electrically insulate one out of an electrically conducting inner electrode position and an electrically conducting outer electrode position of an electrode connection when located therein, and configured with an electrically conducting part configured to conduct current supplied to the other one out of the inner electrode position and the outer electrode position when located therein.

10. The electrode device of claim 9, wherein the first needle electrode and the second needle electrode in an end opposite the attachment end comprises an electrode tip to be arranged at the desired tissue of the mammal.

11. The electrode device of claim 10, wherein the needle electrode comprises an insulating portion and an elongated electrode extending in a longitudinal direction through the insulating portion, wherein the electrode tip is arranged at an end of a first part of the electrode, and wherein a second part of the electrode, opposite the first part and at least partly extended out from the insulating portion, comprises the electrically conducting part.

12. The electrode device of claim 11, wherein the insulating part and the conducting part are arranged parallel in a longitudinal direction and wherein the insulating portion, in a section comprising the insulating part, is twisted to arrange the insulating part at an angle β relative the conducting part.

13. The electrode device of claim 11, wherein the insulating portion consists of an insulating material and comprises one or more protrusions arranged at its envelope surface.

14. The electrode device of claim 9, wherein the first part of the electrode comprises a first conductive alloy providing increased stiffness as compared to a stiffness of the second part, and wherein the second part of the electrode comprises a second conductive alloy providing electrical contact with the electrode connection of the electrode device.

15. The electrode device of claim 1, wherein the handle portion comprises a planar front section, and wherein the first electrode connection and the second electrode connection are arranged in the planar front section such that the first and second needle electrodes when arranged in the respective electrode connection are arranged non-perpendicular to the planar front section.

16. A needle electrode for use in an electrode device for delivery of electrical pulses to a desired tissue of a mammal, wherein the needle electrode comprises an attachment end for releasable attachment to an electrode connection of the electrode device, wherein:

the attachment end is configured with an insulating part configured to electrically insulate one out of an electrically conducting inner electrode position and an electrically conducting outer electrode position of an electrode connection when located therein, and configured with an electrically conducting part configured to conduct current supplied to the other one out of the inner electrode position and the outer electrode position when located therein.

17. The needle electrode of claim 16, wherein the first needle electrode and the second needle electrod in an end opposite the attachment end comprises an electrode tip to be arranged at the desired tissue of the mammal.

18. The needle electrode of claim 17, wherein the needle electrode comprises an insulating portion and an elongated electrode extending in a longitudinal direction through the insulating portion, wherein the electrode tip is arranged at an end of a first part of the electrode, and wherein a second part of the electrode, opposite the first part and at least partly extended out from the insulating portion, comprises the electrically conducting part.

19. The needle electrode of claim 18, wherein the insulating part and the conducting part are arranged parallel in a longitudinal direction and wherein the insulating portion, in a section comprising the insulating part, is twisted to arrange the insulating part at an angle β relative the conducting part.

20. The needle electrode of claim 18, wherein the insulating portion consists of an insulating material and comprises one or more protrusions arranged at its envelope surface.

21. The needle electrode of claim 16, wherein the first part of the electrode comprises a first conductive alloy providing increased stiffness as compared to a stiffness of the second part, and wherein the second part of the electrode comprises a second conductive alloy providing electrical contact with the electrode connection of the electrode device.

* * * * *